United States Patent [19]

Miller et al.

[11] Patent Number: 4,679,947
[45] Date of Patent: Jul. 14, 1987

[54] METHOD AND APPARATUS FOR MEASURING STEAM QUALITY

[75] Inventors: Charles E. Miller; Gerald L. Schlatter, both of Boulder; Louis T. Yoshida, Longmont, all of Colo.

[73] Assignee: Engineering Measurements Co., Longmont, Colo.

[21] Appl. No.: 755,493

[22] Filed: Jul. 16, 1985

[51] Int. Cl.⁴ .................... G01N 9/36; G01K 17/06
[52] U.S. Cl. .................... 374/42; 73/32 A; 73/29
[58] Field of Search .............. 73/32 A, 29, 30, 155; 374/40, 42, 118

[56] References Cited

U.S. PATENT DOCUMENTS

| | | | |
|---|---|---|---|
| 3,100,395 | 8/1963 | Morley | 374/42 |
| 3,516,283 | 6/1970 | Abbotts | 73/32 A |
| 4,034,597 | 7/1977 | Fredriksson | 374/42 |
| 4,096,745 | 6/1978 | Rivkin et al. | 73/32 A |
| 4,149,403 | 4/1979 | Muldary et al. | 73/29 |
| 4,193,290 | 3/1980 | Sustek, Jr. et al. | 73/29 |
| 4,409,825 | 10/1983 | Martin et al. | 73/155 |
| 4,466,272 | 8/1984 | Stanfeld | 73/32 A |
| 4,480,461 | 11/1984 | Ponzi | 73/32 A |
| 4,491,009 | 1/1985 | Ruesch | 73/32 A |
| 4,524,610 | 6/1985 | Fitzgerald et al. | 73/32 A |
| 4,526,480 | 7/1985 | Ward | 73/32 A |
| 4,542,993 | 9/1985 | Mims et al. | 374/42 |
| 4,547,078 | 10/1985 | Long et al. | 374/42 |
| 4,576,036 | 3/1986 | Huang et al. | 73/29 |
| 4,581,926 | 4/1986 | Moore et al. | 73/29 |

*Primary Examiner*—Charles Frankfort
*Assistant Examiner*—Thomas B. Will
*Attorney, Agent, or Firm*—James R. Young

[57] ABSTRACT

A method and apparatus for measuring steam quality of wet or two-phase flowing steam includes a flow-through densitometer comprised of two parallel tubes connected to two common nodes, a vibrator for causing the tubes to vibrate, and a transducer for detecting the frequency and amplitude of the vibrations. A temperature probe detects the temperature of the steam, and a computer is used to monitor the vibrations and temperature and to calculate steam quality. The computer can also be used to control the vibrator. An intake sampler is positioned in a flowing steam line to divert a representative sample of the wet steam into the densitometer. The bulk density of the steam is determined as a function of the fundamental frequency of the densitometer with the steam flowing therethrough, and the steam quality is determined as a function of the bulk density and vapor density, which is a function of temperature.

46 Claims, 8 Drawing Figures

METHOD AND APPARATUS FOR MEASURING STEAM QUALITY

FIELD OF THE INVENTION

The present invention is related generally to steam analysis methods and apparatus, and more particularly to a method and apparatus for determining and monitoring the quality, thus heat or energy content, of steam in steam systems.

DESCRIPTION OF THE PRIOR ART

Steam systems are used primarily in industry to generate and deliver heat to points where the heat energy is put to useful work. The amount of heat energy delivered is, of course, directly related to the amount of work that can be accomplished. Therefore, it is the amount of heat energy delivered by the steam system for which the steam generator must account and for which the steam user must pay. Without an accurate accounting of heat energy delivered, efficient and accurate management of a steam system is really not possible.

Prior to this invention, such steam system management involved many assumptions that really were not much better than guesses. Also, some equipment, such as modern steam turbines, are very complex machines that require sophisticated controls. The condition of steam delivered to such equipment is critical in achieving optimum efficiency and reduced maintenance. Therefore, there is a great need for a practical method or device for measuring and monitoring the heat energy content of flowing steam at various points in steam systems. However, prior to this invention, there were no such practical methods or devices available.

When saturated steam gives up energy, condensation occurs and the basic nature of the steam changes. Rather than being a consistent, homogeneous vapor, as is the case with superheated or saturated steam, wet steam is a mixture of liquid water particles with water vapor. The liquid water particles and the water vapor coexist in the steam system at the same temperature. This condition is known as two-phase flow. As more and more energy is extracted from the wet steam, as occurs in heat exchangers, more and more vapor condenses to water particles until eventually only liquid water remains. At this point, much of the useful energy is extracted from the steam.

The energy or heat content of saturated or supersaturated steam can be determined easily from temperature and/or pressure measurements of the steam system. Unfortunately, the task is not so easy in wet steam systems wherein two-phase flow is encountered. The physics which controls the flow of two-phase fluids, such as wet steam, is not well understood. Simplified mathematical models derived from laws of thermodynamics and fluid mechanics, so useful in predicting flow of single phase liquids and gases no longer applies when two phases coexist.

The distribution of the water liquid particles in a pipe containing wet steam under flowing conditions is very unpredictable and changes with variations in pipe geometry, direction of flow, temperature, and the like. The water particle and water vapor phases flow at different flow velocities with the water particles usually lagging the water vapor. Sometimes there can be a fairly even distribution of small droplets of liquid water flowing in the steam vapor, but at other times the liquid water droplets combine to form large slugs flowing through the pipe. These slugs of liquid water can also be stretched out in churning or turbulent flow to elongated, amorphous masses twisting through the pipe. Also, in some conditions, a thin film of liquid water flows along the interior surfaces of the pipe in combination with the other flow forms described above. These varying and unpredictable flow phenomena present a formidable, and heretofore unsolved, measurement problem. The literature abounds with theoretical dissertations which attempt to treat rather idealistic models of two-phase flow, but unfortunately they are of little consequence or utility to understanding the real world conditions encountered by industry.

The total energy contained in wet steam is equal to the combined energy of the water particle and water vapor phases. Steam quality, Q, defines the ratio by weight of each phase. Thus, the energy or heat content of wet steam systems is a function of the steam quality, where steam quality Q is defined as the ratio of the mass of vapor, $M_v$, contained within a specified volume, $V_o$, to the total mass, $M_t$, of fluids in the steam system.

Since the heat energy in the liquid water particles and the heat energy in the water vapor are both well established functions of temperature, it is theoretically possible to determine the energy contained in a sample of wet steam by acquiring an accurate measurement of steam quality Q. However, prior to this invention, there was no instrument or technique available for determining or measuring steam quality in commercial or industrial steam systems on a reliable and continuous basis. Unable to measure steam quality, many industrial steam systems operate inefficiently, and it is difficult, if not impossible to accurately account for energy usage among a number of steam users on a steam system or to monitor the actual heat energy delivered to a point of use by a steam system.

SUMMARY OF THE INVENTION

Accordingly, it is a general object of this invention to provide a method and apparatus for determining wet steam quality, thus energy in the steam.

Another object of the present invention is to provide a method and apparatus capable of determining steam quality in flowing wet steam systems.

A further object of the present invention is to provide a method and apparatus that can be used in a wet industrial steam distribution system to determine and monitor steam quality at selected points in the system.

A still further object of the present invention is to provide a method and apparatus for determining and monitoring steam quality in an industrial steam distribution system that is accurate, reliable, inexpensive, and easy to use.

Additional objects, advantages, and novel features of the present invention shall be set forth in part in the description that follows, and in part will become apparent to those skilled in the art upon examination of the following or may be learned by the practice of the invention. The objects and advantages of the invention may be realized and attained by means of the instrumentalities and in combinations particularly pointed out in the appended claims.

To achieve the foregoing and other objects and in accordance with the purpose of the present invention as embodied and broadly described herein, the method of this invention may comprise the steps of collecting the wet steam or a representative sample thereof and passing it through a densitometer to determine the bulk density or mass per unit volume of the wet steam, measuring the temperature of the steam and determining vapor density or mass of the vapor phase, and determining steam quality therefrom. The method includes passing the steam through a continuous tube or chamber, causing the chamber to vibrate, determining the fundamental frequency of the vibrating tube or chamber, and determining the bulk density as a function of the fundamental frequency. The method also utilizes a computer for monitoring the temperature and fundamental frequency, calculating and outputting steam quality determinations, and controlling the vibration frequencies. An enhancement of the method includes swaging or reducing the steam pipe to a smaller diameter and stripping liquid film from the interior surface of the steam pipe at the swage to obtain a uniform mixture of vapor and liquid phases at the sampling location.

To further achieve the foregoing and other objects and in accordance with the purpose of the present invention as embodied and broadly described herein and to implement the method of this invention, the apparatus of this invention may comprise a continuous flow through densitometer and temperature sensing device to obtain bulk density and vapor density values necessary to determine steam quality. The densitometer comprises two tubes mounted at common mass end nodes, a magnetic coil for inducing the tubes to vibrate, and strain guages on one of the tubes to measure the vibrations.

A computer is connected to the temperature sensor and to the strain guages to monitor those measurements and to a coil driver control to vary the frequency of vibration through a band that includes the fundamental or resonant frequency of the tubes and connecting structure as the wet steam flows therethrough. The computer also rapidly calculates and outputs steam quality and related data.

The apparatus also includes a sampling structure for diverting a representative sample of wet steam from a main steam system pipe for flowing the sample through the densitometer chambers and reinjecting it into the steam pipe. A pipe reducer or swage coupling swage and film stripper are positioned in the main steam pipe immediately upstream from the sampler for enhancing a thorough mixture of the liquid and vapor phases at the sampling location.

BRIEF DESCRIPTION OF THE DRAWINGS

The accompanying drawings, which are incorporated in and form a part of the specifications, illustrate a preferred embodiment of the present invention, and together with the description serve to explain the principles of the invention. In the drawings.

DETAILED DESCRIPTION OF THE PREFERRED EMBODIMENTS

Figure 1:
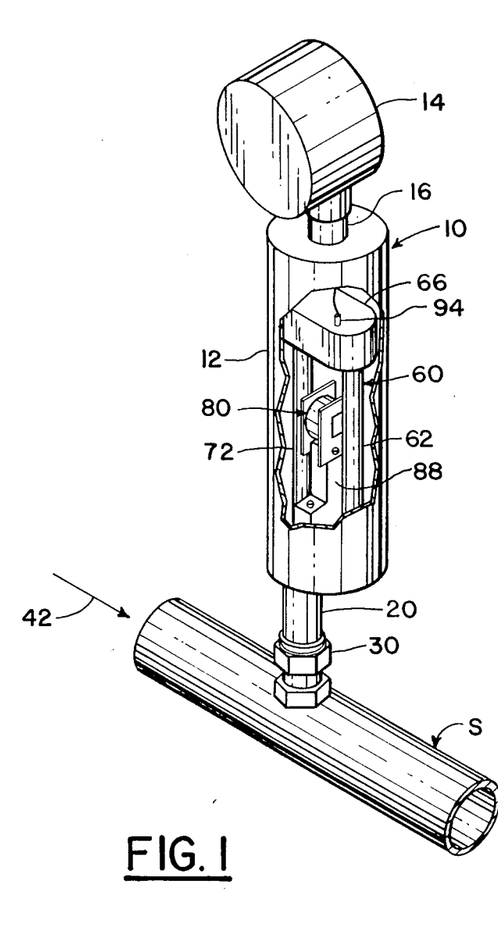
FIG. 1 is a perspective view of the steam quality meter of the present invention with portions of the body thereof cut away to reveal the components inside.

A steam quality meter 10 according to the present invention is shown in FIG. 1 attached to a steam flow line S in a typical steam distribution system. In order to appreciate the method and apparatus of this invention for determining and monitoring steam quality, thus heat or energy content, in a wet steam system where two-phase fluid flow is encountered, it is helpful to review the theory underlaying this invention.

As discussed in the background section above, the heat energy in the liquid water phase and the heat energy in the water vapor phase are well-established functions of temperature and of the masses of those phases. Steam quality Q is an expression of the relation of the masses of the liquid and vapor phases, thus the total heat energy of the wet steam is a function of the steam quality Q. Therefore, if steam quality Q for wet flowing steam can be measured accurately, then the heat energy in the wet flowing steam can be determined accurately by utilizing known enthalpy relationships.

Steam quality Q for a volume $V_o$ of wet steam is defined as the ratio of the mass of vapor $M_v$ contained within the volume $V_o$ to the total mass $M_t$ of the fluids in that volume. Thus:

$$Q = \frac{M_v}{M_t} = \frac{M_v}{M_v + M_L} \quad (1)$$

The method and apparatus of this invention makes use of the density relationship between the liquid and vapor phases and the bulk density of all the fluid in the volume to determine steam quality Q. The bulk density $\bar{\rho}$ of the wet steam is defined as follows:

$$\bar{\rho} = M_t/V_o \quad (2)$$

Since the total mass $M_t$ is equal to the sum of the mass of the vapor $M_v$ plus the mass of the liquid $M_L$ then:

$$\bar{\rho} = \frac{M_v + M_L}{V_o} = \frac{M_v}{V_o} + \frac{M_L}{V_o} \quad (3)$$

The volume occupied by each phase is also important, and the relationship between the volume of the vapor $V_v$ and the total volume $V_o$ can be expressed as the "void fraction" $\alpha$, as follows:

$$\alpha = V_v/V_o \quad (4)$$

Since the total volume $V_o$ is the sum of the liquid volume $V_L$ and the vapor volume $V_V$, then $$V_o = V_L + V_V \quad (5)$$

and $$V_L = V_o - V_V \quad (6)$$

From equation (4), $$V_V = \alpha V_o, \quad (7)$$

therefore, combining equations (6) and (7), $$V_L = V_o - \alpha V_o = (1-\alpha)V_o. \quad (8)$$

Since density is defined as mass per unit volume, then $$\rho_L = \frac{M_L}{V_L} \text{ and } \rho_v = \frac{M_v}{V_v} \quad (8.1)$$

Therefore, the liquid mass $M_L$ and the vapor mass $M_V$ in terms of density are $$M_L = \rho_L V_L \text{ and } M_v = \rho_v V_v \quad (8.2)$$

and, in terms of total volume $V_o$, $$M_L = \rho_L(1-\alpha)V_o \quad (9)$$

and $$M_v = \rho_v \alpha V_o \quad (10)$$

Equations (9) and (10) show the relationships $$M_L/V_o = \rho_L(1-\alpha) \quad (11)$$

and $$M_v/V_o = \rho_v \alpha \quad (12)$$

Combining equations (11) and (12) with equation (3) provides a definition of bulk density $\bar{\rho}$ in terms of the void fraction $\alpha$, as follows:

$$\bar{\rho} = \rho_v \alpha + (1-\alpha)\rho_L = \rho_v \alpha + \rho_L - \alpha \rho_L \quad (13)$$

Therefore, $$\bar{\rho} - \rho_L = \alpha(\rho_v - \rho_L) \quad (14)$$

and the void fraction $\alpha$ in terms of density is $$\alpha = \frac{\bar{\rho} - \rho_L}{\rho_v - \rho_L} \quad (15)$$

Then, combining the relationships in equations (9) and (10) with the steam quality Q of equation (1), $$Q = \frac{\rho_v \alpha V_o}{\rho_v \alpha V_o + \rho_L(1-\alpha)V_o} = \frac{\rho_v \alpha}{\rho_v \alpha + \rho_L(1-\alpha)} \quad (16)$$

Finally, substituting equation (15) into equation (16) to eliminate the void fraction yields an expression for steam quality Q solely in terms of density, as follows:

$$Q = \frac{\rho_V}{\rho_V - \rho_L} - \frac{\rho_V}{\bar{\rho}}\left(\frac{\rho_L}{\rho_V - \rho_L}\right) \quad (17)$$

If the liquid density $\rho_L$ is always very large compared to the vapor density $\rho_v$, i.e., $\rho_L >> \rho_v$, a very useful simplification of equation (17) results, as follows:

$$Q = \frac{O}{O - \rho_L} - \frac{\rho_V}{\bar{\rho}}\left(\frac{\rho_L}{O - \rho_L}\right) = \frac{\rho_V}{\bar{\rho}} \quad (18)$$

The result is that steam quality Q is effectively defined as the ratio of the vapor density $\rho_v$ to the bulk or average density $\bar{\rho}$.

Fortunately, for purposes of this invention, the vapor density $\rho_v$ and liquid density $\rho_L$ are well-established functions of the temperature T. While the precise functional relationships are mathematically complex, they are easily handled by microcomputers providing realtime measurement of steam vapor density $\rho_v$ and liquid density $P_L$.

The principle variable in the steam quality Q determination is the bulk density $\bar{\rho}$. Theoretically, the best method of determining bulk density $\bar{\rho}$ is to weigh a fluid of known volume. Unfortunately, conventional weighing techniques have not been successfully applied to two-phase flowing fluids, such as wet steam, except under rather ideal laboratory conditions. The problem is further compounded where such weight measurements are attempted on flowing two phase fluids where the phase distributions are constantly changing and where the individual phases are moving at different velocities in the system.

The method and apparatus of this invention solve these problems and provide efficient, accurate, and relatively easy effective measurement of the bulk density $\bar{\rho}$, of the flowing two-phase wet steam by use of physical principles of vibrating beams. This invention, therefore, includes a vibration densitometer arrangement for obtaining a bulk density value for use along with the temperature T, vapor density $\rho_v$, and liquid density $P_L$ relationships to derive a value for steam quality Q.

Figure 6:
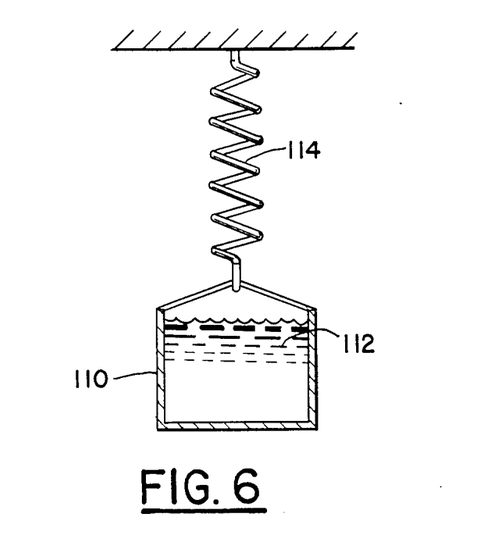
FIG. 6 is a simple mechanical oscillating system used in describing the operating theory of this invention.

In a simple model such as that illustrated in FIG. 6, comprised of a container 110 of mass $M_c$ containing a fluid 112 having a mass $M_f$ suspended on a spring 114 having a spring constant K, the container 110 will oscillate in a simple harmonic motion. A direct application of Newton's law to such a simple harmonic system shows that the frequency of vibration f is inversely proportional to the square root of the mass $M_c$ of the container 110 and the mass $M_f$ of its fluid contents 112. Thus:

$$f = \left[\frac{K}{M_c + M_f}\right]^{\frac{1}{2}} \quad (19)$$

From equation (2), the bulk density, $\bar{\rho}$, is defined as:

$$\bar{\rho} = M_t/V_o$$

Thus, where the mass of the total fluid $M_t$ in equation (3) is the equivalent of the mass of the fluid 112 in the container 110 $M_f$ in equation (19), and substituting:

$$f = \left[\frac{K}{M_c + \bar{\rho}V_o}\right]^{\frac{1}{2}} \quad (20)$$

Expanding equation (20) and solving for bulk density $\bar{\rho}$ yields:

$$\bar{p} = \frac{k}{f^2 V_o} - \frac{M_c}{V_o} \qquad (21)$$

By defining a variable $A = K/V_o$ and a variable $B = M_c/V_o$ and substituting into equation (21), the result yields an expression for bulk density, $\bar{p}$, as a function of frequency, f, as follows:

$$\bar{p} = A/f^2 + B \qquad (22)$$

Thus, equation (22) is a basic law which describes a vibrating type densitometer. Since frequency f can be measured with extreme precision, there is significant appeal in using this relationship to determine density by measuring frequency. However, to be of practical value for measuring density of a flowing fluid, a flow-through container is almost essential.

Figure 7:
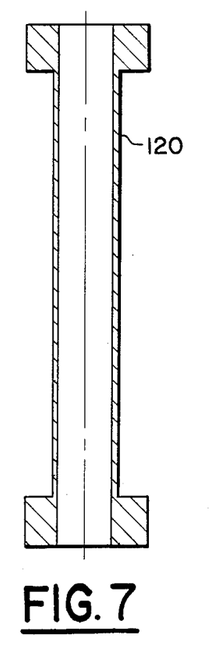
FIG. 7 is an elongated tubular container used in describing the operating theory of this invention.
Figure 8:
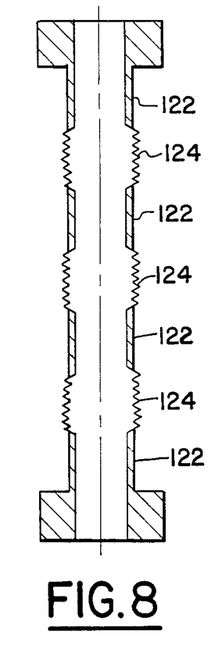
FIG. 8 is a conceptual representation of an elongated tubular container divided into individual sections used to describe the operating theory of this invention.

A hollow tube such as the tube 120 shown in FIG. 7, can be used as a simplified flow-through container for purposes of this theoretical analysis. In a simplified sense, for comparison with the mechanical oscillating systems shown in FIG. 6, the length of a hollow tube 120 can be analyzed as being comprised of a series of individual containers 120 coupled together with flexible sections or bellows 124, as illustrated in FIG. 8. Thus, each tube section 122 in FIG. 8 is analogous to the container 110 in FIG. 6, and each flexible section or bellows 124 in FIG. 8 is analogous to the spring 114 in FIG. 6. Essentially, each tube container 122 in FIG. 8 being suspended by a bellows 124 is capable of simple harmonic motion similar to the container 110 suspended by spring 114 in FIG. 6. However, unlike the single container model of FIG. 6, the entire structure in FIG. 8 can be made to vibrate at a number of discreet frequencies (harmonics) and modes.

According to a mathematical model based on calculus and differential equations, the specifics of which are not necessary for the purposes of this explanation, the sizes of the tube section containers 122 and bellows 124 can be decreased and their numbers increased to infinite, where they are mathematically equivalent to the solid length of tube 120 in FIG. 7. In the infinite limit, therefore, the model in FIG. 8 is mathematically identical to the model in FIG. 7. Thus, the tube 120 in FIG. 7 functions like both the bellows 124 in FIG. 8 and the spring in FIG. 6.

While appearing to be rigid, the tube 120 is really elastic and will deflect under a load in a very predictable manner, as does the more familiar helical spring 114. The primary difference is that the deflection of the tube 120 is very small and imperceptible to the human eye. This difference in magnitude of deflections, however, does not affect the validity of the mathematical and physical equations that describe the oscillation or vibration of the tube 120. In fact, the fundamental physical laws that govern the dynamic behavior of the single container model in FIG. 6 are equally valid with respect to the tube model of FIG. 7. Therefore, the bulk density $\rho$ of the fluid in the tube has a direct effect on the frequency at which the tube 120 vibrates under a load. Specifically, as shown in equation (22), the bulk density $\bar{p}$ is inversely proportional to the square of the frequency, i.e., $f^2$. Thus, by measuring the resonant frequency f of the vibrating tube 120, a value for the bulk density $\bar{p}$ of the fluid in the tube can be determined. As mentioned above, the frequency f of vibration can be measured very accurately, thus a very accurate determination of bulk density $\bar{p}$ can be determined by measuring the resonant frequency f of the vibrating tube 120.

Since the densities of the liquid and vapor phases ($\rho_L$, $\rho_v$) can be determined from temperature T of the steam, as discussed above, and bulk density of the fluid can now be determined from the resonant frequency of vibration f of the tube 120. Then, from equation (18), the quality Q of the steam can be determined. Therefore, the quality Q of the wet steam can be determined by monitoring steam temperature T and frequency of resonant vibration f of the tube 120.

It is significant to mention that steam vapor temperature is a function of its pressure for saturated steam. Therefore, while this description of the invention focuses primarily on temperature measurements to determine vapor density $\rho_v$, it should be understood that such determination can be made from pressure measurements as well. Thus, the use of pressure to determine vapor density $\rho_v$ is considered to be the equivalent of the uses of temperature for this purpose in this invention.

One of the most important advantages to the use of frequency of vibration f of a flow-through tube 120 in determing steam quality Q is speed of response. For example, with the tube 120 vibrating at approximately 4,000 Hz, rapid changes in mass of the two-phase wet steam fluid flowing in the tube 120 are immediately translated into changes of resonant frequency f that can be detected and measured in milliseconds with great precision.

Another important consideration is that since the total mass of a two-phase fluid in a wet steam system is relatively small, extraordinary sensitivity is required to detect small changes in fluid phase concentrations. Large acceleration fields present in the vibrating tube 120 means that relatively large force changes are generated for small changes in mass. The greater the acceleration, the greater the force. Thus, small changes in the two-phase fluid mass are detectable with extreme accuracy by measuring the resulting more dramatic changes in frequency of the vibrating tube 120.

With the above theoretical discussion of the principles utilized by this invention in mind, it is appropriate to now describe the specific method and apparatus of this invention used to determine steam quality Q thus heat or energy content, of a two-phase flowing wet steam system. Essentially, this method and apparatus use the fundamental or harmonic frequency of a tube having two-phase fluid flowing therethrough along with the temperature of the fluid, to determine the steam quality Q of the fluid.

Figure 2:
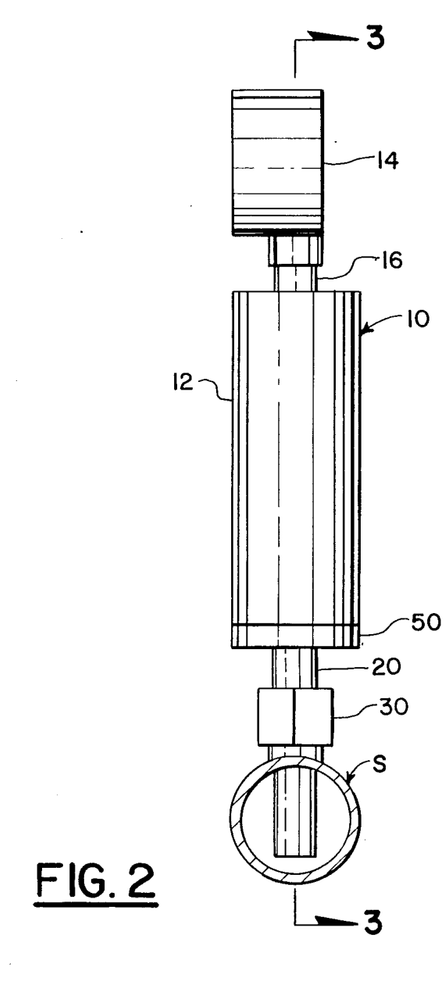
FIG. 2 is a side elevation view of the steam quality meter of the present invention.

The steam quality meter apparatus 10 according to the present invention is shown in FIGS. 1 and 2 mounted on a conventional steam system flow line S. It is comprised of a vibrating tube type densitometer 60 enclosed in a cylindrical housing 12. Two-phase fluid from the steam flow line S is conducted to the densitometer 60 by the stand pipe 20, which extends into the interior of the steam flow line S and is mounted thereon by a swage loc coupling 30. An electrical component compartment 14 is mounted by a neck tube 16 to the housing 12.

Figure 3:
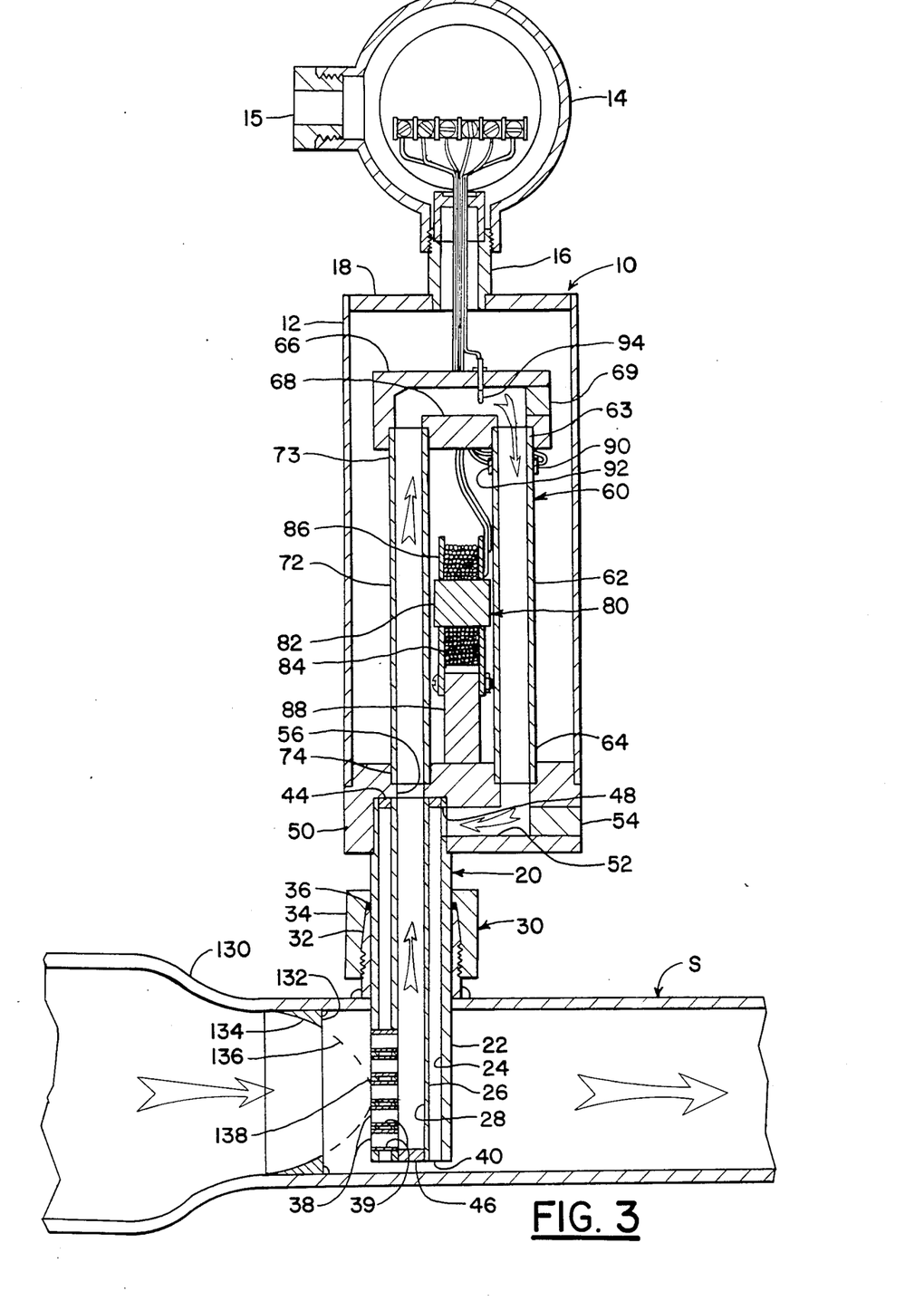
FIG. 3 is an enlarged cross-section view of the steam quality meter of the present invention taken along lines 3—3 of FIG. 2.

The cross-sectional view in FIG. 3 shows the structure and functional features of the steam quality meter 10 of the present invention in more detail. The steam quality meter 10 utilizes a densitometer 60 comprised of twin hollow tubes 62, 72, rigidly fixed at each end. The steam samples from the steam flow line S flows continuously through these tubes 62 72. The tubes are forced to resonate, in a similar fashion to that of a tuning fork, creating an acceleration force on all matter within the tubes 62, 72, regardless of whether it is liquid, gas, or solid. Consequently, each particle of mass within the tubes 62, 72, exerts, in turn, a force which is proportional to the product of its mass and acceleration, i.e., Force=Mass X Acceleration.

As the total mass or bulk density within the tubes 62, 72 increases, the resonant frequency decreases by the relationship shown in equation (22) above. The constants A and B in equation (22) are determined by calibration of the device. Thus, a measure of resonant frequency of the tubes results in a measure of the total mass or bulk density. Then, with a precision measurement of the steam temperature by temperature probe 94, the device determines the vapor density or the mass that would exist if tubes were full of saturated steam. That theoretical vapor density is the same for any vapor that exists in the system under that temperature and pressure. Thus, the vapor density $\rho_v$ of the vapor in the two phase flow is also determined by the temperature or pressure measurement. The ratio of the vapor density to the bulk density of the wet steam is the steam quality Q.

Referring primarily to FIG. 3 therefore, the steam quality meter 10 is comprised of a cylindrical housing 12 enclosed on the top by a cover plate 18 and on the bottom by a base block 50. The densitometer 60 of the present invention is positioned inside this cylindrical housing 12. A neck 16 extending through the top cover plate 18 supports a cylindrical container 14 that is utilized primarily to house the electronic components of the steam quality meter 10. The outlet plug 15 in container 14 accommodates the passage therethrough of the necessary electrical wires (not shown) for connecting the electronics of the steam quality meter to a power source, as well as to desired peripheral control and monitoring equipment, as will be described in more detail below.

The densitometer assembly 60 is essentially comprised of two vertical parallel tubes 62, 72 positioned in the housing 12 a spaced distance apart from each other. These tubes 62, 72 are rigidly mounted in separate conduit 52, 56, respectively, in base block 50. They are also rigidly mounted at their tops in a crossover head 66 having a conduit 68 therethrough that connects the tube 62 with the tube 72. This arrangement is designed to conduct a flow of two-phase wet steam from the steam flow pipe S upwardly through tube 72, through the crossover head 66, and downwardly through tube 62 and back to the steam flow line S, all as indicated by the flow arrows in FIG. 3.

This densitometer assembly 60 also includes a magnetic coil 80 mounted on a pedestal 88 between the tubes 62, 72. This magnetic coil is comprised of a metallic core 82 and a set of wire windings 84 positioned in a spool 86 around the core 82. A pair of strain guages 90, 92 preferably coil-type, are mounted on the upper end of tube 62, and a temperature probe 94 is positioned in the crossover head 66 to measure the temperture of the two-phase fluid flowing through the conduit 68 therein.

The densitometer tubes 62, 72, are connected to the steam flow line S by the stand pipe 20. The stand pipe 20 is uniquely designed to continuously collect a representative sample of the two-phase fluid flowing through the steam pipe S that accurately reflects average steam quality. It also creates extreme turbulence, hence mixing, of the steam liquid and vapor phases in the sample. The steam sample flows continuously through the densitometer tubes 72, 62, and then returns to the steam flow pipe S.

As best seen in FIG. 3, the structure of the stand pipe 20 is in the form of a double tube arrangement having an outer tube 22 with a smaller diameter inner tube 26 positioned concentrically therein. The inner tube is small enough in diameter to leave an annulus 24 between the outer tube 22 and the inner tube 26. A top plug 44 closes and seals the top of the annulus 24 from the interior 28 of the inner tube 26 at the top. A bottom plug 46 is also positioned in the bottom of inner tube 26 to close the bottom end thereof. The inside flow conduit 28 of the inner pipe 26 is aligned in fluid flow relation with the conduit 56 adjacent the bottom of tube 72 The annulus 24 is connected in fluid flow relation to conduit 52 through an appropriately positioned hole 48 near the upper end of the outer tube 22.

A plurality of inlet holes 38 through the lower end of the outer tube 22 are connected by small transverse tubes 39 to the interior 28 of inner tube 26. These inlet holes 38 are distributed across the cross-section of the steam flow pipe S in order to admit into the inner tube 26 a representative sample of the two-phase fluid flow in the steam flow pipe S. The admitted two-phase fluid then flows upwardly through the inner tube 26 into the first densitometer tube 72. From the first densitometer tube 72 the fluid flows through the conduit 68 in crossover head 66 and downwardly through the second densitometer tube 62, all as illustrated by the flow arrows in FIG. 3. The two-phase fluid then continues to flow out of the bottom 64 of the second densitometer tube 62, through the conduit 52, and into the annulus 24. The two-phase fluid then exits from the annulus 24 through the opening 40 at the bottom thereof to return into the main stream fluid flow in the steam pipe S.

It is appropriate to mention at this point that the flow direction through the densitometer could be reversed with the steam flowing upwardly through the annulus 24, through tube 62 then 72 and out through inner tube 26. The discharge of fluid out the bottom 40 or 46, as the case may be, into the main stream of steam has the effect of continuing the flow of steam through the densitometer 60 utilizing the well-known effect of Bernoulli's Law to draw the steam sample through the densitometer 60.

The stand pipe 20 can be mounted in the steam flow pipe S in any conventional manner. In this illustration it is shown mounted by a swage loc-type connector having a tapered sleeve 32 welded to the steam flow pipe S. An inside tapered nut 34 screwed onto the sleeve 32 frictionally locks the outer tube 22 in place therein and tightens a seal 36 around the connection thereof.

The continuous flow sampler arrangement described above is designed to provide an isothermal sample of two-phase fluid flow that is representative in proportions of fluids and temperature of the main steam flow in pipe S. To enhance the accuracy and unformity of the sample, it is helpful to pre-condition the flow to provide a more uniform mixture of the liquid and vapor phases flowing in the main steam pipe S at the position where the steam sample is taken.

Therefore, another significant component of this invention is the choke and film stripper shown in the main steam pipe S in FIG. 3. The main steam flow is choked first by the pipe reducer or swage coupling 130, which reduces the inside diameter of the main steam line S.

The film stripper 132 is located at the small diameter end of the swage 130. The film stripper is in the shape of an annular ring affixed to the inside surface of the steam pipe S. Its interior surface 134 is curved to converge inwardly toward its downstream end. This structure is effective to strip and divert the liquid film phase that typically follows the interior surface of the steam pipe S away from the surface and into the main steam flow in the center of the pipe S where it is thoroughly mixed with the rest of the steam.

It is preferred, although not considered necessary, to shape the interior curved surface 134 of the film stripper 132 in the form of a segment of a parabolic figure of revolution, as shown in FIG. 3. The inlet openings 30 of sampler pipe 20 are then preferably positioned in the area of the apex 138 of the parabolic extension 136 of surface 134, where mixture uniformity is at an optimum. In this manner, an even more uniform sample of the two-phase steam can be obtained.

The cylindrical housing 12, top plate 18, and base 50 form an enclosed chamber around the densitometer. This chamber can be evacuated to allow the densitometer to function virtually independently of ambient temperature and pressure conditions around the device 10.

Figure 4:
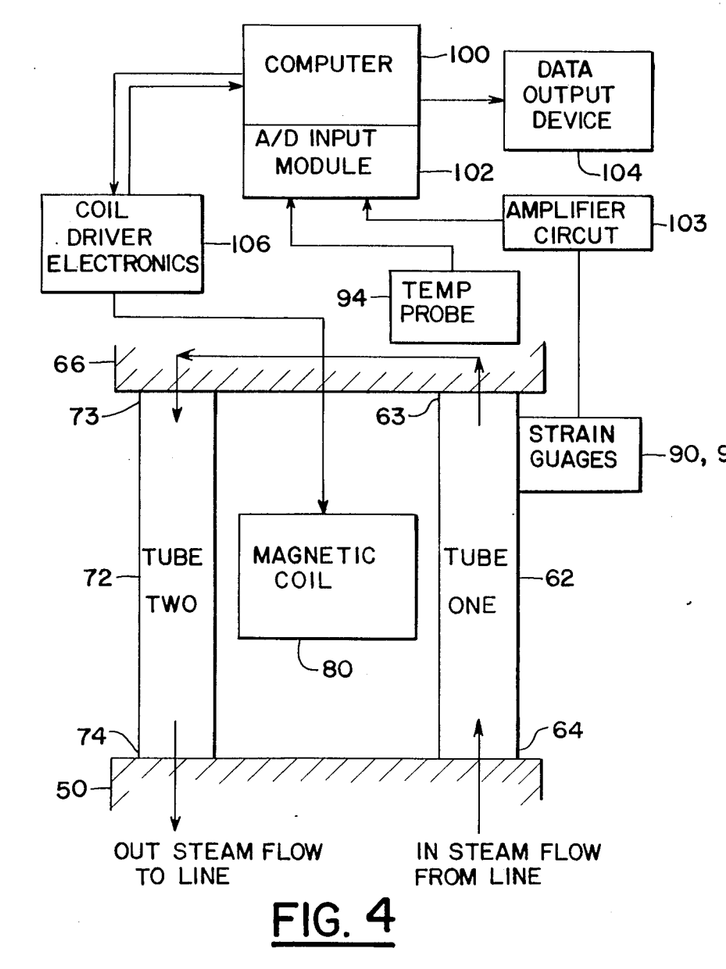
FIG. 4 is a logic diagram of the control circuit of the steam quality meter of the present invention.

The operation of the steam quality meter of the present invention is best described with reference to the combination of FIGS. 3 and 4, wherein FIG. 4 is a logic diagram of the control circuit of the steam quality meter. As described above, a representative sample of the two-phase fluid flow in the steam line S is collected through the plurality of holes 38 in the stand pipe 20. This representative sample of the two-phase fluid flows from there upwardly through the first densitometer tube 72 and downwardly through the second densitometer tube 62. As the fluid is flowing through the densitometer tubes 62, 72, the coil driver electronics 106 powers and drives the magnetic coil 80 with an oscillating current. The result is that the magnetic coil 80 imparts energy to cause a vibrating motion in the metallic densitometer tubes 62, 72. The magnitude and frequency of the vibration of tube 62 is detected by the strain guages 90, 92. The strain guage output is directed to a computer 100. Simultaneously, the temperature probe 94 in the crossover conduit 68 measures the temperature of the fluid flowing therethrough. The output of the temperature probe is also directed to the computer 100.

It is significant to note in FIGS. 3 and 4 that the two tubes 62, 72 are anchored at their respective bottom ends 64, 74 to a common block mass 50. Likewise, they are both anchored at their respective upper ends 63, 73 to a common crossover head mass 66. The benefit of this configuration is that the densitometer 60 is completely symmetrical with a common node or mass at each end of both tubes. The result is that the entire densitometer system 60 is completely balanced symmetrically so that there are no distortions in the fundamental or harmonic frequency of the system that could otherwise result from asymmetrical arrangements, and it is essentially isothermal in its function. The actual result is therefore an averaging of the vibration effect between the two tubes 62, 72, which results in an extremely accurate fundamental frequency measurement as a function of the bulk density of the fluid flowing through the tubes. Assymetrical arrangements would yield less accurate results.

It should be noted that while the magnetic coil described above is the preferred method of imparting vibration to the metallic tubes, other methods of imparting energy to the tubes to cause vibrations can be used. For example, the tubes could be struck with an impact device to impart vibrations thereto, or, a broad band noise could also be generated in the vicinity of the tubes to impart energy thereto. These latter two methods would, of course, be more effective where non-metallic tubes are used. The principle feature utilized in this invention is that energy is imparted to the tubes in some manner to cause vibrations thereof and a detection of the fundamental or harmonic frequency of the system. The fundamental frequency is then combined with the temperature of the fluid to determine the steam quality.

As described in the theoretical analysis above, the fundamental or harmonic frequency f of the tube is a function of the mass of the fluid flowing through the tube 62, 72. For example, in a prototype of the densitometer shown in FIG. 3, the fundamental or harmonic frequency of the tube varies between approximately 2,700 Hz for a liquid water-filled tube to approximately 4,500 Hz for an evacuated tube. Therefore, in the embodiment shown in FIG. 4, the computer 100 is connected to the coil driver electronics 106 in such a manner that the computer can control the frequency of the field generated by the magnetic coil 80.

During start-up, the computer is programmed to cause the magnetic coil 80 to vibrate the tubes 62, 72, throughout the band of frequencies between 2,700 Hz and 4,500 Hz. As the frequency of vibrations sweep across this range of 2,700 Hz to 4,500 Hz, the strain gauges 92 continuously monitor the vibrating frequency of the tube and the magnitude of the vibration displacement.

According to the physical laws that govern the system, the vibrations of the tube are at maximum displacement where the magnetic coil 80 is driving the system at the fundamental or harmonic resonant frequency of the densitometer tubes 62, 72 and the interconnecting structure. The strain guage output can be in a variety of forms, depending on the particular strain guage selected; however, in a conventional strain guage the output is usually in the form of voltage. Therefore, when the tubes 62, 72 and interconnecting structure are vibrating at the structure's fundamental or harmonic frequency, the voltage output of the strain guage is at a maximum. Since the strain guage output is usually analog, it is necessary to equip the digital computer 100 with an input module 102 that has the capability of accepting analog signals and converting such analog signals to digital form for use by the computer. The same capability is generally required for input from the temperature probe 94, which is also usually in the form of an analog voltage of varying magnitude, depending on the temperature being sensed by the probe.

Thus, as described above, by driving the magnetic coil to sweep a frequency band between the 2,700 Hz for liquid water to 4,500 Hz for an evacuated tube and by monitoring the magnitude of the displacements in the vibrating tube with the strain guage, the fundamental or harmonic frequency of the densitometer tubes 62, 72 and connecting structure with two-phase fluid flowing therethrough can be detected quickly. As mentioned above, the change of fundamental or harmonic frequency in relation to a change in the density of the fluid flowing therethrough is extremely sensitive and easy to measure, and any changes in the density of the fluid flowing therethrough can be detected almost immediately very accurately by detecting the change of the fundamental or harmonic frequency of the densitometer structure 60.

In the embodiment described in FIG. 4, it has been found beneficial to program the computer to drive the magnetic coil to sweep a band of frequencies very rapidly, and preferably at a rate of approximately four sweeps of the band range per second. Also, it has been found preferable to program the computer to narrow the frequency band through which the magnetic coil 80 sweeps when the fundamental or harmonic frequency of the system is determined.

Of course, the extent to which the band is narrowed and the rate at which the band is narrowed is a matter of design choice. However, it has been found that once the fundamental or harmonic frequency of the system is determined, the band can be narrowed almost immediately to a 20 Hz band covering approximately 10 Hz on each side of the fundamental frequency of the system. This 20 Hz band is therefore constantly changed and adjusted as the fundamental frequency, i.e., density of the fluid flowing through the tubes, changes.

In the event there would be a rapid, high magnitude fluctuation of fluid density so that the fundamental frequency would move outside this 20 Hz band quicker than the four sweeps per second can detect, then the computer is programmed to again widen the band out to the limits of 2,700 Hz for liquid water and 4,500 Hz for an evacuated tube. When this maximum band is swept again, the fundamental frequency of the system will be detected very quickly so that the band can again be narrowed to the 20 Hz band of 10 Hz on either side of the new actual fundamental frequency.

Utilizing this data of the fundamental frequency of the vibrating system, which is a function of the bulk density as described above, in combination with the temperature of the fluid flowing through the system, which is a function of the vapor density of the system as described above, the steam quality Q can be computed according to the mathematical relationships described above.

Actually, several adjustments of system variables and constants should be considered in calibrating and operating the system for obtaining more accurate results or output. For example, the values of the constants A and B in equation (22) above can be determined empirically when calibrating the system. They are functions of the physical structure, dimensions, and mass of the particular system being used and normally do not vary once they are set.

As mentioned above, the temperature probe 94 is preferably a platinum temperature sensor, which varies in electrical resistance (ohms) in relation to steam temperature. Such changes in resistance can be measured from voltage variations according to the basic OHm's law $V=IR$. The actual temperature can then be determined mathematically in terms of degrees Fahrenheit or centigrade, as desired, from the resistance. For example, the temperature in degrees Fahrenheit can be determined according to the following equation:

$$T = 32 + 1.8*(-b+SQRT(b*b-4*a*c))/(2*a) \quad (23)$$

where T=Temperature in degrees F., $a = -6.0188220000E-7$, $b = 3.8101882200E-3$, and $c = 1-\text{Resistance}/1000$.

In the preferred embodiment described above, the coil type strain guage is used to measure the frequency and magnitude of the vibrations of the tube. This kind of strain guage uses the carrier technique of exciting a bridge circuit to vary the output voltage. The voltage output is then amplified by an amplifier circuit 103 for feeding into the computer 100 for performing the above-described calculations.

Once the temperature of the steam is obtained, the vapor density $\rho_v$ and liquid density $\rho_L$ can be obtained from a standard table of saturated steam characteristics.

It is also known that the vibration characteristics of the densitometer structure 60 will vary or change over wide ranges of temperature variations. Therefore, it is desirable for more accurate results to compensate the actual frequency of the densitometer for such temperature variations. Such compensation can be made mathematically according to the following formula:

$$f_c = f_d + b_2(T_o - T) \quad (24)$$

where $f_c$ is the temperature compensated frequency, $f_d$ is the actual measured densitometer frequency, $b_2$ is a constant that is a function of temperature, $T_o$ is a standard or base temperature for purposes of calibration, and T is the temperature in degrees F. as determined above. The bulk density $\overline{\rho}$ can then be determined from equation (22), and steam quality Q can be determined very accurately from equation (18).

Since the steam quality Q is effectively a ratio of the mass or density of the vapor to the bulk mass or density at the point of the sample at any time, the actual energy of wet steam two-phase flow can be determined, if desired, from the respective enthalpies of the vapor and liquid phases, which are functions of temperature as will be readily apparent to persons skilled in the art. desired.

Such energy calculations are basically mathematical operations, thus they are not part of this invention. However, a computer can be programmed to perform such calculations very rapidly and concurrently with its monitoring functions and can output the energy flow along with the steam quality data through a conventional data output device 104, such as a printer. In this manner, with the use of the steam quality meter 10 and the method of this invention, the steam quality of a two-phase wet steam system can be monitored continuously at any selected point in the steam flow distribution system so that there is a constant awareness and continuous, accurate record of the heat or energy distributed and delivered by the steam system to the various user points.

Figure 5:
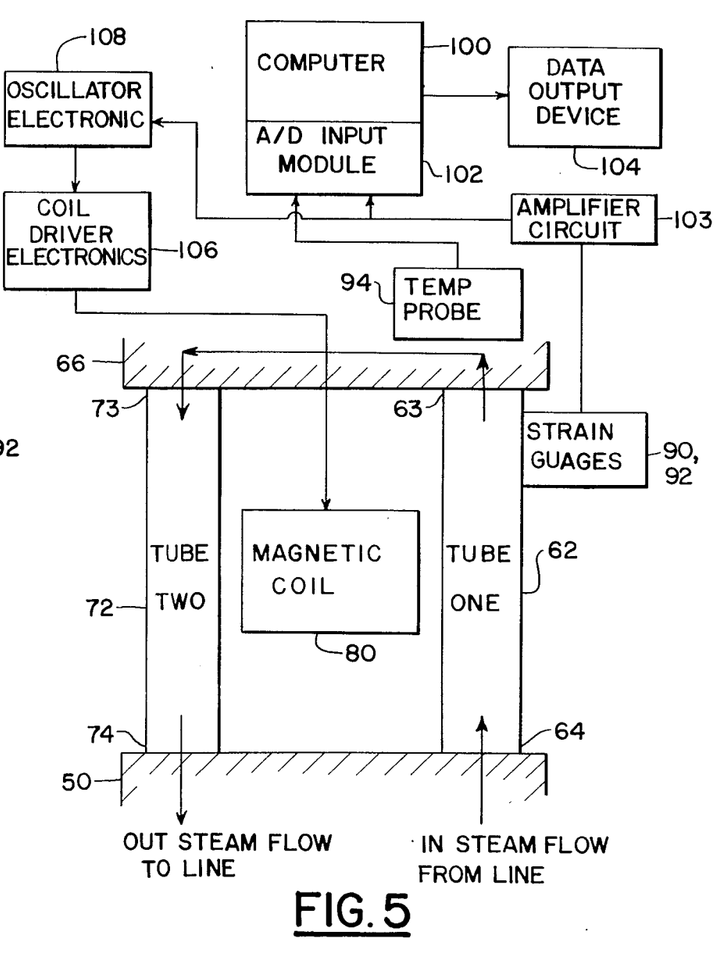
FIG. 5 is a logic diagram of an alternative control circuit for the steam quality meter of the present invention.

An alternative embodiment is shown in the logic diagram of FIG. 5. This system is similar to that shown in FIG. 4 with the exception that an oscillator electronic circuit 108 is positioned between the strain guages 90, 92 and the coil driver electronics 106. In this arrangement, the system seeks automatically the fundamental frequency of the vibrating system and simultaneously drives the magnetic coil at the fundamental frequency. The strain guage output is also fed into the computer 100 to monitor and utilize the fundamental frequency of the system.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention defined by the claims which follow.

The embodiments of the invention in which an exclusive property or privilege is claimed are defined as follows:

1. Apparatus for determining steam quality of wet steam flowing in a steam line, comprising:
   densitometer means connected to said steam line for measuring the bulk density of the wet steam flowing in the steam line;
   temperature measuring means connected to said steam line for measuring the temperature of the wet steam flowing in the steam line; and
   computer means connected to said densitometer means and to said temperature measuring means programmed to output steam quality of the wet steam as a ratio of the temperature to the bulk density measurements.

2. The apparatus of claim 1, wherein said densitometer means includes flow-through chamber means for continuously conducting a flow of wet steam through said densitometer means, vibration inducing means for causing said chamber means to vibrate, and vibration measuring means for measuring the frequency of vibration of the vibrating chamber means.

3. The apparatus of claim 2, including vibration measuring means for measuring the amplitude of vibration of the vibrating chamber means.

4. The apparatus of claim 3, including computer means for monitoring and measuring the resonant frequency of said vibrating chamber and for determining the bulk density of the wet steam from said resonant frequency.

5. The apparatus of claim 4, wherein said vibration inducing means includes driver means for driving said vibration inducing means at varying frequencies.

6. The apparatus of claim 5, including computer means for controlling said driver means to sweep said vibration inducing means through frequency bands that include the resonant frequency of said chamber means.

7. The apparatus of claim 6, wherein said vibration inducing means includes magnetic coil means for causing said chamber to vibrate.

8. The apparatus of claim 2, wherein said flow through chamber means includes two cylindrical tubes, each of which is rigidly connected at one end to a common first mass and at the opposite end to a common second mass.

9. The apparatus of claim 8, wherein said two cylindrical tubes are comprised of the same material and are substantially equal in length, diameter, and thickness to each other and are positioned in substantially parallel, spaced apart relation to each other.

10. The apparatus of claim 9, wherein said first mass has a conduit extending therethrough, which connects said respective one ends of said two tubes in fluid flow relation to each other, and said second mass has conduits therein for conducting steam flow into and out of said chamber means.

11. The apparatus of claim 1, including sampler means connected to said densitometer means for continuously collecting and diverting a sample flow of steam from a steam system pipe and directing the sample flow into said densitometer means.

12. The apparatus of claim 11, wherein said sampler means includes a first tube positioned to extend transversely through the steam system pipe, said first tube having a plurality of inlet openings therein directed into the flow of steam in the pipe and distributed evenly across the cross-section of the pipe.

13. The apparatus of claim 12, including a second tube of smaller diameter than the first tube positioned inside said first tube, the interior of one of said first and second tubes being connected to said inlet openings for conducting the sample fluid to the densitometer and the interior of the other of said first and second tubes being connected to said densitometer and having an outlet opening into said pipe for conducting the sample out of the densitometer and back into the pipe.

14. The apparatus of claim 11, including film stripper means positioned in the pipe in close upstream proximity to said sampler means for diverting liquid from the interior wall of the pipe into the steam flow in the center of the pipe to effect mixing of the liquid and vapor phases of the wet steam.

15. The apparatus of claim 14, wherein said film stripper means includes an annular collar positioned around the interior wall of the pipe and having an inside surface inclined inwardly toward its downstream side.

16. The apparatus of claim 14, wherein said inside surface is in the shape of a segment of a parabola.

17. The apparatus of claim 15, wherein said stripper means and said sampler means are spaced from each other a distance such that the sampler is positioned at about the apex of the parabolic extension of said inside surface of said collar.

18. The apparatus of claim 17, including reducing means in said pipe upstream adjacent said collar for reducing the diameter of the pipe to converge the wet steam flow therein into said collar.

19. Apparatus for measuring the bulk density of a flowing two phase fluid, comprising:
   two parallel tubes, each of said tubes having a first end and a second end with the first ends of the respective tubes being adjacent each other and the second ends of the respective tubes being adjacent each other;
   first common mass means positioned at the first ends of said tubes for providing a common first node for said first ends of said tubes, the first ends of said tubes being rigidly anchored to said first common mass means;
   second common mass means positioned at the second ends of said tubes for providing a common second node for said second ends of said tubes, the second ends of said tubes being rigidly anchored to said second common mass means;
   conduit means connected to said tubes for directing the flowing two phase fluid through said tubes;
   vibration inducing means positioned between said tubes for causing said respective tubes to vibrate in opposition to each other while said two phase fluid is flowing therethrough; and
   vibration measuring means associated with said tubes for measuring the frequency of vibration of the tubes.

20. The apparatus of claim 19, including computer means connected to said vibration measuring means for detecting and monitoring the resonant frequency of said tubes and for rapidly calculating the bulk density of the two-phase fluid.

21. The apparatus of claim 19, wherein said conduit means includes a first flow passage connecting the first end of one of said tubes to a two-phase fluid source, a second flow passsage connecting the respective second ends of said tubes together in fluid flow relation to each other, and a third fluid passage connecting the first end of the other tube to a disposal place for said fluid.

22. The apparatus of claim 21, wherein said third fluid passage connects the first end of said other tube to the two-phase fluid source for disposal therein.

23. The apparatus of claim 21, wherein said second flow passage extends through said second common mass means.

24. The apparatus of claim 23, wherein said two parallel tubes and said first and second mass means are sized and shaped to form a symmetrical unit in terms of mass and dimension.

25. The method of determining steam quality of flowing two phase wet steam, comprising the steps of:
   flowing the wet steam through a chamber;
   inducing the chamber structure to vibrate;
   measuring the resonant frequency of the chamber with the wet steam therein, and determining the bulk density of the wet steam as a function of the resonant frequency of the chamber structure;
   measuring the wet steam temperatue in the chamber, and determining the vapor density as a function of the temperature; and
   determining steam quality as a ratio of the vapor density to the bulk density of the wet steam.

26. The method of claim 25, including the step of inducing the chamber to vibrate by actuating an electromagnet with an oscillating current adjacent the chamber structure.

27. The method of claim 25, including the step of inducing the chamber to vibrate by generating a broad band noise in the proximity of the chamber structure.

28. The method of claim 25, including the step of inducing the chamber to vibrate by striking the chamber with an object.

29. The method of claim 26, including the steps of driving the electromagnet to oscillate and vibrate the chamber through a band of frequencies that includes within its limits the resonant frequency of the chamber.

30. The method of claim 29, including the step of driving the oscillations and vibrations through a band that has a minimum lower frequency limit defined by the resonant frequency of the chamber with a vacuum therein and a maximum upper frequency limit defined by the resonant frequency of the chamber full of water.

31. The method of claim 30, including the step of narrowing said band of frequencies to more narrowly bracket the actual resonant frequency of the chamber with wet steam flowing therethrough.

32. The method of claim 30, including the step of shifting the limits of the band upwardly and downwardly in increments corresponding to changes in the resonant frequency of the chamber with wet steam flowing therethrough in order to maintain said resonant frequency in the middle of said band.

33. The method of claim 32, including the step of widening said band to said minimum lower limit and said maximum upper limit when the resonant frequency moves outside the narrowed band.

34. The method of claim 33, including the step of varying the oscillation frequency to sweep across said band about four times per second.

35. The method of claim 26, including the step of driving the electromagnet to oscillate at the resonant frequency of the chamber with wet steam flowing therethrough.

36. The method of claim 25, including the steps of flowing the wet steam through a chamber comprised of two adjacent tubes having their respective ends anchored in common node masses with each other.

37. The method of claim 36, including the step of measuring the resonant frequency of the chamber by attaching a strain guage coil to one of said tubes and directing the output of the strain gauge coil to a computer for monitoring the vibrating characteristics of the chamber and for determining resonant frequency.

38. The method of claim 25, including the step of collecting a representative sample of flowing wet steam in a steam pipe and directing the sample to flow through the chamber.

39. The method of claim 38, including the step of positioning an inlet conduit across the cross-section of the steam pipe with a plurality of openings therein directed into the steam flow and distributed across the cross-section of the steam pipe.

40. The method of claim 39, including the step of positioning an annular collar having an inclined surface in the interior of the pipe immediately upstream from the inlet with the inclined inner surface converging toward the center of the pipe.

41. The method of claim 40, including the steps of shaping the inclined inner surface in the shape of a segment of a parabola and positioning the collar a spaced distance upstream from the inlet such that the apex of the parabolic extension of the surface corresponds to the location of the inlet.

42. The method of claim 41, including the step of reducing the steam pipe to a smaller size immediately upstream of the collar.

43. Apparatus for measuring steam quality of flowing wet steam on a real-time basis, comprising:
   two hollow elongated tubes of the same size and shape positioned in parallel relation spaced apart from each other, wherein one end of one tube is connected together in fluid flow relation to the adjacent end of the other tube and the opposite ends of both tubes are anchored in a common mass;
   vibration inducing means positioned between said tubes for causing said tubes to vibrate in respectively opposite directions from the vibrations in the other such that there is a node of no vibration at the connection of one tube to the other and another node of no vibration in the common mass;
   an inlet flow line connected in fluid flow relation to the end of one of said tubes that is anchored in the common mass, and an outlet flow line connected in fluid flow relation to the end of the other of said tubes that is anchored in the common mass, such that there is a continuous flow path for fluid extending from said inlet flow line through one of said tubes and then through the other of said tubes and out the outlet flow line;
   vibration sensing means connected to one of said tubes for sensing the frequency and magnitude of vibrations of said tube;
   temperature sensing means in said flow path for sensing the temperature of a fluid flowing in the flow path; and
   computer means connected to said vibration sensing means and to said temperature sensing means for determining resonant frequency of the vibrating tube and outputting the steam quality value as a ratio of the temperature to the resonant frequency.

44. The apparatus of claim 43, wherein said inlet flow line and said outlet flow line are connected to said common mass in concentric relation to each other.

45. The apparatus of claim 44, wherein said inlet and outlet flow lines extend in concentric relation to each other into a flow pipe of wet steam and the inlet steam flow line has a plurality of inlet openings distributed across a cross section of the flow pipe of wet steam, and including a film stripper sleeve attached to the steam flow line converging axially inwardly toward a point in the steam flow line through which said concentric inlet and outlet flow lines extends.

46. The apparatus of claim 44, including driver means connected to said vibration inducing means for driving said vibration inducing means at varying frequencies and wherein said computer means is connected to said driver means and is programmed to control said driver means to cause said vibration inducing means through frequency bands that include the resonant frequency of the tube with steam flowing therethrough and to narrow the band around the resonant frequency when the resonant frequency becomes more stable and to widen the band when the resonant frequency falls outside the band.

* * * * *